(12) United States Patent
Natal, Jr.

(10) Patent No.: US 11,185,437 B2
(45) Date of Patent: Nov. 30, 2021

(54) TESTICLE COVERING CONDOM ASSEMBLY

(71) Applicant: Jorge Natal, Jr., Hollywood, FL (US)

(72) Inventor: Jorge Natal, Jr., Hollywood, FL (US)

( * ) Notice: Subject to any disclaimer, the term of this patent is extended or adjusted under 35 U.S.C. 154(b) by 0 days.

(21) Appl. No.: 16/853,369

(22) Filed: Apr. 20, 2020

(65) Prior Publication Data

US 2021/0322203 A1  Oct. 21, 2021

(51) Int. Cl.
*A61F 6/04* (2006.01)

(52) U.S. Cl.
CPC .......... *A61F 6/04* (2013.01); *A61F 2006/047* (2013.01)

(58) Field of Classification Search
CPC ...... A61F 2006/047; A61F 6/04; A61F 6/065; A61F 2006/042; A61F 6/146; Y10S 128/918; A61H 19/32
See application file for complete search history.

(56) References Cited

U.S. PATENT DOCUMENTS

| | | | |
|---|---|---|---|
| 3,759,254 A | 9/1973 | Clark | |
| 5,111,831 A | 5/1992 | Foggia | |
| 5,314,447 A | 5/1994 | Papurt | |
| 5,718,236 A | 2/1998 | Curcio | |
| D400,247 S | 10/1998 | Landberg | |
| 6,061,840 A * | 5/2000 | Alligator | A41B 9/002 2/400 |
| 6,209,543 B1 | 4/2001 | Star | |
| 6,478,027 B1 | 11/2002 | Serrano | |
| 8,839,792 B2 * | 9/2014 | Brunner | A61F 6/04 128/844 |
| 2004/0094163 A1 | 5/2004 | Benson | |
| 2005/0028825 A1 * | 2/2005 | McCoy | A61F 6/04 128/844 |

* cited by examiner

*Primary Examiner* — Ophelia A Hawthorne

(57) ABSTRACT

A testicle covering condom assembly for protecting a user's penis and scrotum from sexually transmitted diseases includes a condom that is wearable on a user's penis for protection during sexual intercourse. A sack is coupled to and extends away from the condom for containing the user's scrotum when the condom is worn. Additionally, the sack is comprised of a resiliently stretchable material to accommodate varying sizes of scrotums. A pair of arms is each of the arms is coupled to the condom and each of the arms is positioned outside of the sack. Each of the arms extends along opposite sides of the sack to limit the possible diameter of the sack thereby inhibiting the sack from sliding downwardly on the scrotum.

6 Claims, 5 Drawing Sheets

TESTICLE COVERING CONDOM ASSEMBLY

(b) CROSS-REFERENCE TO RELATED APPLICATIONS

Not Applicable

(c) STATEMENT REGARDING FEDERALLY SPONSORED RESEARCH OR DEVELOPMENT

Not Applicable

(d) THE NAMES OF THE PARTIES TO A JOINT RESEARCH AGREEMENT

Not Applicable

(e) INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

(f) STATEMENT REGARDING PRIOR DISCLOSURES BY THE INVENTOR OR JOINT INVENTOR

Not Applicable

(g) BACKGROUND OF THE INVENTION

(1) Field of the Invention

The disclosure relates to condom devices and more particularly pertains to a new condom device for protecting a user's scrotum and penis from sexually transmitted diseases.

(2) Description of Related Art Including Information Disclosed Under 37 CFR 1.97 and 1.98

The prior art relates to condom devices including a variety of condoms with a sack integrated therein for containing a user's scrotum. In each case the sack and the condom are a unitary structure. In at least one case a ring is provided that is positionable around the sack for retaining the scrotum in the sack. The prior art discloses a condom with a scrotum opening extending therethrough thereby facilitating a scrotum to be passed through the condom when the condom is worn. The prior art discloses a condom that includes a tail for positioning between a user's buttocks when the condom is worn.

(h) BRIEF SUMMARY OF THE INVENTION

An embodiment of the disclosure meets the needs presented above by generally comprising a condom that is wearable on a user's penis for protection during sexual intercourse. A sack is coupled to and extends away from the condom for containing the user's scrotum when the condom is worn. Additionally, the sack is comprised of a resiliently stretchable material to accommodate varying sizes of scrotums. A pair of arms is each of the arms is coupled to the condom and each of the arms is positioned outside of the sack. Each of the arms extends along opposite sides of the sack to limit the possible diameter of the sack thereby inhibiting the sack from sliding downwardly on the scrotum.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

(I) BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

(j) DETAILED DESCRIPTION OF THE INVENTION

Figure 1:
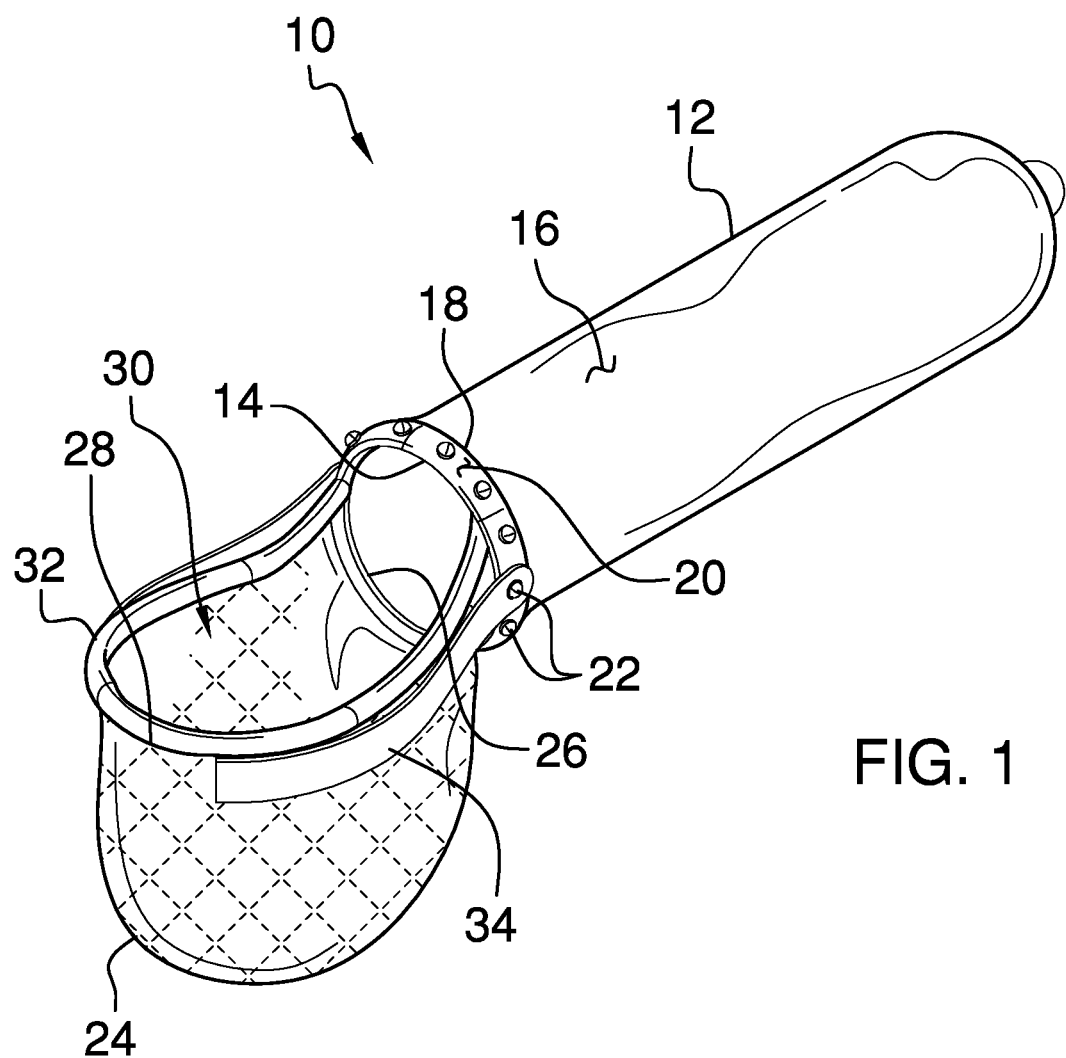
FIG. 1 is a top perspective view of a testicle covering condom assembly according to an embodiment of the disclosure.
Figure 2:
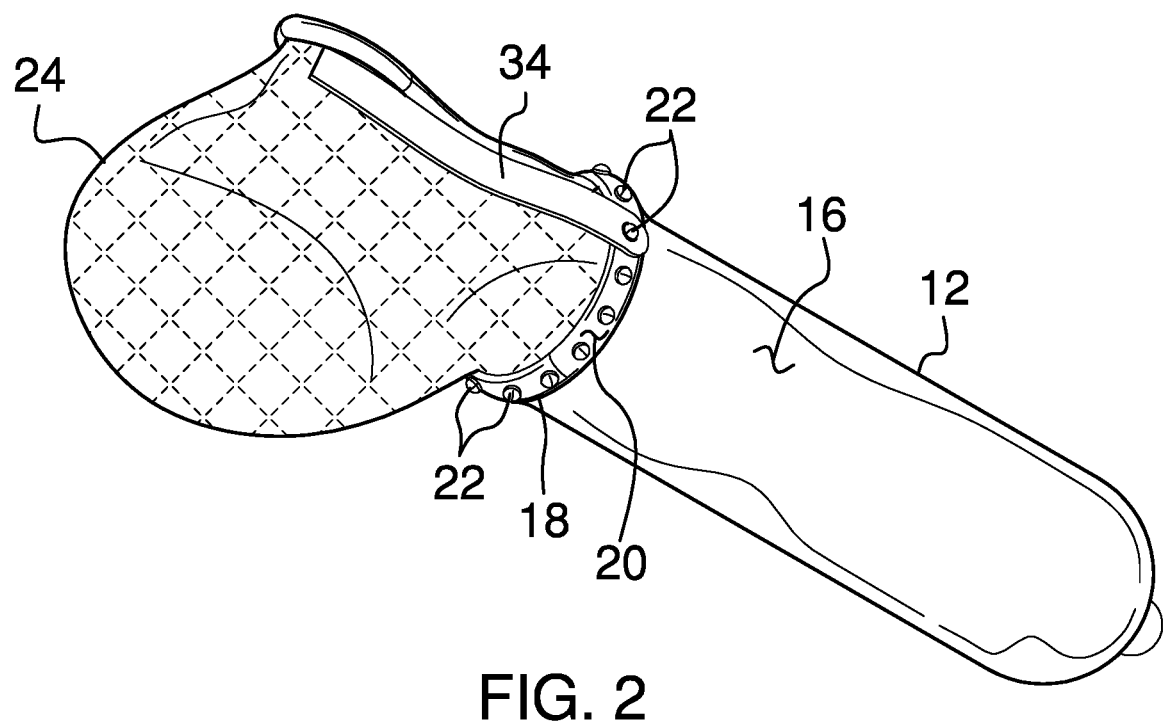
FIG. 2 is a bottom perspective view of an embodiment of the disclosure.
Figure 3:
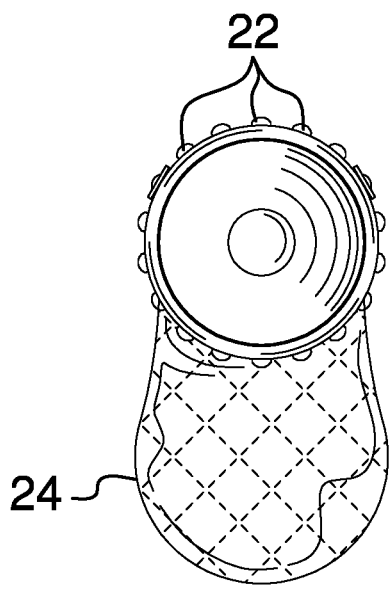
FIG. 3 is a front view of an embodiment of the disclosure.
Figure 4:
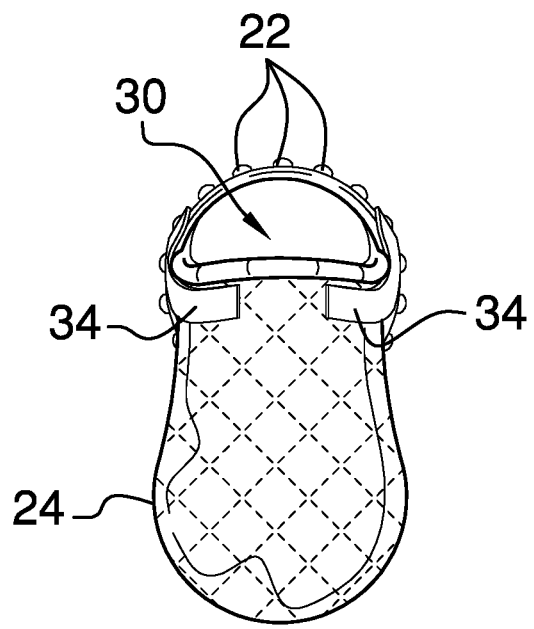
FIG. 4 is a back view of an embodiment of the disclosure.
Figure 5:
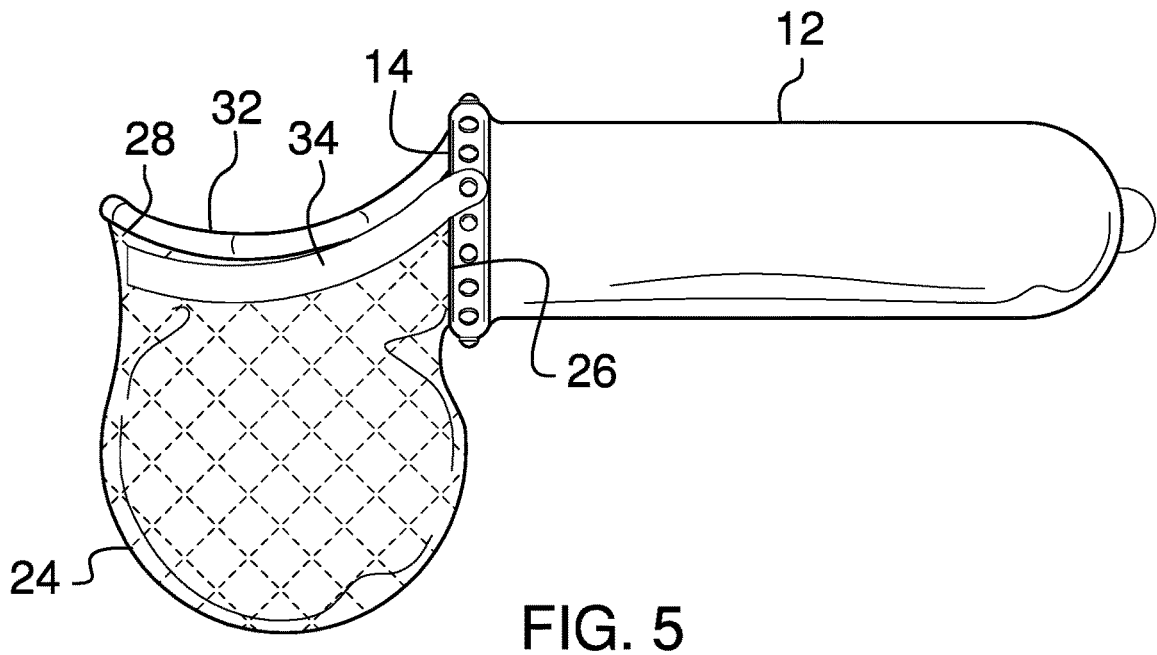
FIG. 5 is a left side view of an embodiment of the disclosure.
Figure 6:
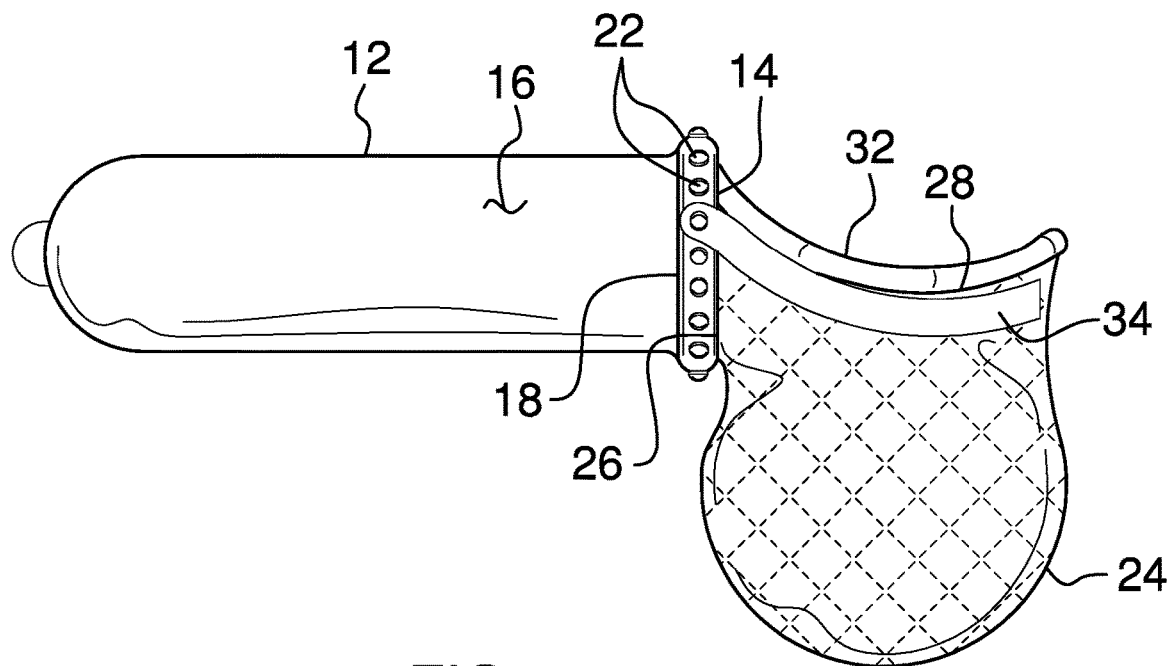
FIG. 6 is a right side view of an embodiment of the disclosure.
Figure 7:
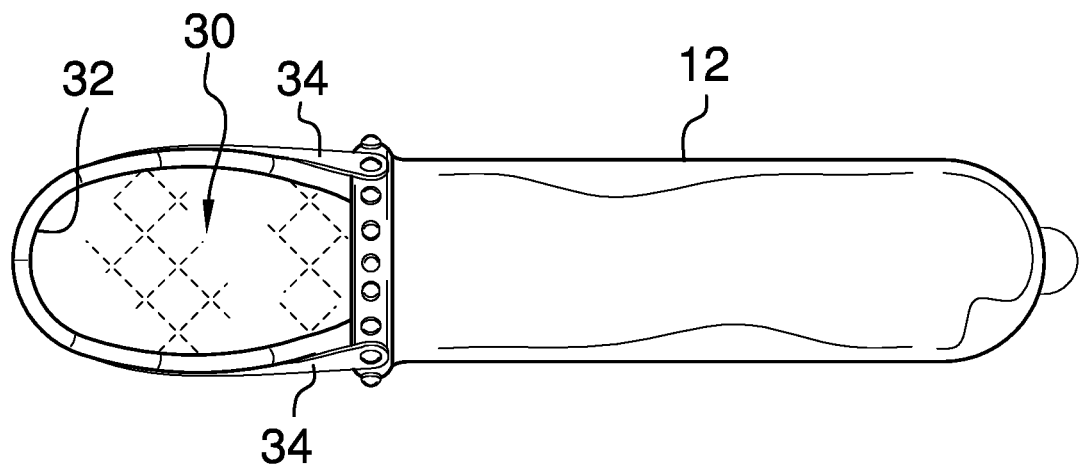
FIG. 7 is a top view of an embodiment of the disclosure.
Figure 8:
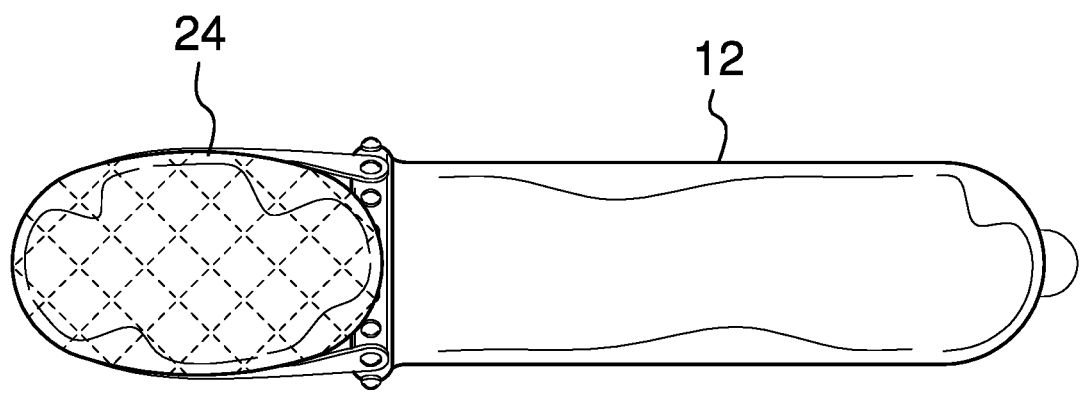
FIG. 8 is a bottom view of an embodiment of the disclosure.

With reference now to the drawings, and in particular to FIGS. 1 through 8 thereof, a new condom device embodying the principles and concepts of an embodiment of the disclosure and generally designated by the reference numeral 10 will be described.

As best illustrated in FIGS. 1 through 8, the testicle covering condom assembly 10 generally comprises a condom 12 that is wearable on a user's penis for protection during sexual intercourse. The condom 12 is comprised of a fluid impermeable material to protect the user's penis from sexually transmitted diseases. Additionally, the condom 12 has an open end 14 that is open into an interior of the condom 12 and the condom 12 has an outer surface 16. A band 18 is coupled around the condom 12, and the band 18 is aligned with and surrounds the open end 14. Moreover, the band 18 is positioned on the outer surface 16 and the band 18 has an outwardly facing surface 20 with respect to the condom 12. A plurality of nubs 22 is each coupled to the outwardly facing surface 20 of the band 18. The nubs 22 are spaced apart from each other and are distributed around a full circumference of the band 18.

A sack 24 is coupled to and extends away from the condom 12 to contain the user's scrotum when the condom 12 is worn. The sack 24 is comprised of a fluid impermeable material to protect the user's scrotum from sexually transmitted diseases. Additionally, the sack 24 is comprised of a resiliently stretchable material to accommodate varying sizes of scrotums. The sack 24 has a forward edge 26 and a top edge 28, and the forward edge 26 is coupled to the open end 14 of the condom 12 having the forward edge 26 extending partially around a circumference of the open end 14.

The top edge 28 intersects the open end 14 at opposite sides of the open end 14. The top edge 28 is oriented to extend rearwardly away from the open end 14 of the condom 12 to define an opening 30 into the sack 24 for receiving the scrotum. A rib 32 is coupled to the top edge 28 of the sack 24 and the rib 32 extends along a full length of the top edge 28. The rib 32 is thickened with respect to the sack 24 for retaining the sack 24 in place when the condom 12 is worn.

A pair of arms 34 is each coupled to the band 18 and each of the arms 34 is positioned outside of the sack 24. Each of the arms 34 extends along opposite sides of the sack 24 to limit the possible diameter of the sack 24. In this way each of the arms 34 inhibits the sack 24 from sliding downwardly on the scrotum. Each of the arms 34 is biased toward each other. Moreover, each of the arms 34 is comprised of a resiliently bendable material thereby facilitating the arms 34 to be urged away from each other during fitment of the sack 24. Each of the arms 34 engages a respective one of the nubs 22 on the band 18.

In use, the condom 12 is worn prior to engaging in sexual intercourse and the user's scrotum is positioned in the sack 24. In this way both the user's penis and the user's scrotum are protected from sexually transmitted diseases. Additionally, the arms 34 and the rib 32 on the sack 24 inhibit the sack 24 from sliding downwardly on the user's scrotum during sexual intercourse. In this way the user's scrotum is protected during the entire duration of sexual intercourse. The condom 12 and the sack 24 are discarded after engaging in sexual intercourse.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A testicle covering condom assembly for covering a user's scrotum as well as the user's penis for protection against sexually transmitted diseases, said assembly comprising:

a condom being wearable on a user's penis for protection during sexual intercourse, said condom being comprised of a fluid impermeable material wherein said condom is configured to protect the user's penis from sexually transmitted diseases, said condom has an open end being open into an interior of said condom;

a band being coupled around said condom;

a sack being coupled to and extending away from said condom wherein said sack is configured to contain the user's scrotum when said condom is worn, said sack being comprised of a fluid impermeable material wherein said sack is configured to protect the user's scrotum from sexually transmitted diseases, said sack being comprised of a resiliently stretchable material wherein said sack is configured to accommodate varying sizes of scrotums, said sack having a forward edge and a top edge, said forward edge being coupled to said open end of said condom having said forward edge extending partially around a circumference of said open end, said top edge intersecting said open end at opposite sides of said open end, said top edge being oriented to extend rearwardly away from said open end of said condom to define an opening into said sack for receiving the scrotum; and a pair of arms, each of said arms being coupled to said band, each of said arms being positioned outside of said sack, each of said arms extending along opposite sides of said sack to limit the possible diameter of said sack Wherein each of said arms is configured to inhibit said sack from sliding downwardly on the scrotum.

2. The assembly according to claim 1, wherein:

said condom has an open end being open into an interior of said condom, said condom having an outer surface; and said band is aligned with and surrounds said open end, said band being positioned on said outer surface, said band having an outwardly facing surface with respect to said condom.

3. The assembly according to claim 2, further comprising a plurality of nubs, each of said nubs being coupled to said outwardly facing surface of said band, said nubs being spaced apart from each other and being distributed around a full circumference of said band.

4. The assembly according to claim 1, further comprising a rib being coupled to said top edge of said sack, said rib extending along a full length of said top edge, said rib being thickened with respect to said sack for retaining said sack in place when said condom is worn.

5. A testicle covering condom assembly for covering a user's scrotum as well as the user's penis for protection against sexually transmitted diseases, said assembly comprising:

a condom being wearable on a user's penis for protection during sexual intercourse, said condom being comprised of a fluid impermeable material wherein said condom is configured to protect the user's penis from sexually transmitted diseases, said condom having an open end being open into an interior of said condom, said condom having an outer surface;

a band being coupled around said condom, said band being aligned with and surrounding said open end, said band being positioned on said outer surface, said band having an outwardly facing surface with respect to said condom;

a sack being coupled to and extending away from said condom wherein said sack is configured to contain the user's scrotum when said condom is worn, said sack being comprised of a fluid impermeable material wherein said sack is configured to protect the user's scrotum from sexually transmitted diseases, said sack being comprised of a resiliently stretchable material wherein said sack is configured to accommodate varying sizes of scrotums;

a pair of arms, each of said arms being coupled to said band, each of said arms being positioned outside of said sack, each of said arms extending along opposite sides of said sack to limit the possible diameter of said sack wherein each of said arms is configured to inhibit said sack from sliding downwardly on the scrotum;

a plurality of nubs, each of said nubs being coupled to said outwardly facing surface of said band, said nubs being spaced apart from each other and being distributed around a full circumference of said band; and wherein each of said arms is biased toward each other, each of said arms being comprised of a resiliently bendable material thereby facilitating said arms to be urged away from each other during fitment of said sack, each of said arms engaging a respective one of said nubs on said band.

6. A testicle covering condom assembly for covering a user's scrotum as well as the user's penis for protection against sexually transmitted diseases, said assembly comprising:

a condom being wearable on a user's penis for protection during sexual intercourse, said condom being comprised of a fluid impermeable material wherein said condom is configured to protect the user's penis from sexually transmitted diseases, said condom having an open end being open into an interior of said condom, said condom having an outer surface;

a band being coupled around said condom, said band being aligned with and surrounding said open end, said band being positioned on said outer surface, said band having an outwardly facing surface with respect to said condom;

a plurality of nubs, each of said nubs being coupled to said outwardly facing surface of said band, said nubs being spaced apart from each other and being distributed around a full circumference of said band;

a sack being coupled to and extending away from said condom wherein said sack is configured to contain the user's scrotum when said condom is worn, said sack being comprised of a fluid impermeable material wherein said sack is configured to protect the user's scrotum from sexually transmitted diseases, said sack being comprised of a resiliently stretchable material wherein said sack is configured to accommodate varying sizes of scrotums, said sack having a forward edge and a top edge, said forward edge being coupled to said open end of said condom having said forward edge extending partially around a circumference of said open end, said top edge intersecting said open end at opposite sides of said open end, said top edge being oriented to extend rearwardly away from said open end of said condom to define an opening into said sack for receiving the scrotum;

a rib being coupled to said top edge of said sack, said rib extending along a full length of said top edge, said rib being thickened with respect to said sack for retaining said sack in place when said condom is worn; and a pair of arms, each of said arms being coupled to said band, each of said arms being positioned outside of said sack, each of said arms extending along opposite sides of said sack to limit the possible diameter of said sack wherein each of said arms is configured to inhibit said sack from sliding downwardly on the scrotum, each of said arms being biased toward each other, each of said arms being comprised of a resiliently bendable material thereby facilitating said arms to be urged away from each other during fitment of said sack, each of said arms engaging a respective one of said nubs on said band.

* * * * *